United States Patent [19]

Barber

[11] Patent Number: 4,523,582

[45] Date of Patent: Jun. 18, 1985

[54] DEVICE FOR SUSPENDING THE HUMAN BODY IN AN INVERTED POSITION

[76] Inventor: S. Morgan Barber, 1417 La Habra, Lake San Marcos, Calif. 92069

[21] Appl. No.: 386,011

[22] Filed: Jun. 7, 1982

[51] Int. Cl.[3] ............................................... A61F 5/00

[52] U.S. Cl. ..................................... 128/71; 272/144; 272/145

[58] Field of Search ............................ 128/25, 51-52, 128/44, 69-71, 75, 80 R; 272/62-63, 93, 94, 96, 134, 142, 144, 145, 119, 109, 70; 280/11.3; 36/107-109; 2/22

[56] References Cited

U.S. PATENT DOCUMENTS

| | | | |
|---|---|---|---|
| 1,422,683 | 7/1922 | Eltgroth | 36/136 |
| 2,214,052 | 9/1940 | Good | 272/96 |
| 2,786,512 | 3/1957 | Moyer | 128/71 |
| 3,380,447 | 4/1968 | Martin | 128/75 |
| 3,589,358 | 6/1971 | Megal | 128/71 |
| 4,072,317 | 2/1978 | Pommerening | 280/11.3 X |
| 4,132,424 | 1/1979 | Olivieri | 280/11.3 |

*Primary Examiner*—Richard J. Apley
*Assistant Examiner*—Chris Coppens
*Attorney, Agent, or Firm*—B. F. Spencer

[57] ABSTRACT

A high-top, form-fitting shoe is disclosed for suspending the human body in an inverted position. The shoe includes a re-enforcing member located in the heel-arch area of the shoe. An inverted U-shaped member, spanning the top portion of the shoe, is pivotally attached to the re-enforcing plate on each side of the shoe adjacent the arch area. The under side of the U-shaped member is spaced apart from the top portion of the shoe to prevent physical contact therewith. A hook member is rigidly attached at the apex of the inverted U-shaped member. The hook is held in front of the leg of the user by a holding means such as a strap. When inverted, the user is suspended from the shoe, the weight of the user being carried from the shoe into the re-enforcing plate, to the inverted U-shaped member and onto the hook. The hook is removably attachable to a horizontal supporting bar. The location of the pivot axis of the inverted U-shaped member upon the re-enforcing plate is selected to insure that the weight of the human body acting upon the hook extends along a line perpendicular to the pivot axis and through the approximate center of gravity of the human body of the user when the user is in the inverted position.

10 Claims, 14 Drawing Figures

DEVICE FOR SUSPENDING THE HUMAN BODY IN AN INVERTED POSITION

BACKGROUND OF THE INVENTION

The present invention relates to the suspension of the human body in an inverted position and, in particular, to a device into which the feet of the user may be comfortably secured for supporting the human body in an inverted position.

Inclined and inverted suspension of the human body is well known and has been used to treat a variety of physical ailments. Inclined or inverted suspension has been found to relax muscle tension, relieve stress upon bones and muscles, improve circulation of the blood in parts of the body, and reduce or moderate nervous disorders. Physicians and chiropractors employ patient inversion, as well as traction, for the treatment of a number of back problems. Inversion therapy is also employed to develop amd strengthen certain muscles in the body, as by exercising.

A number of machines have been developed for tilting or rotating a patient about a horizontal axis from a normal or upright body position into an inclined or inverted position while maintaining the patient secured to the machine. This may be achieved by holding the patient's thighs, calves, legs, ankles, heels, insteps or shoulders. Examples of such machines are disclosed in U.S. Pat. Nos. 1,085,486; 1,693,810; 2,934,063, 3,081,085; 3,152,802; 3,286,708; 3,380,447; 3,568,669; 3,589,358; 3,707,285; 4,114,613; as well as in my U.S. Pat. No. 4,232,662.

Certain of the prior art machines possess a number of serious disadvantages. Clamping the patient around the leg and above the ankle as by stocks, straps or leg cuffs, even though padded, causes trauma to the patient. To reduce this problem, certain machines have been designed to provide padded clamps fitted behind the ankle and in front of the foot at the instep area. Other machines provide a heel brace with a formed member placed over the top of the foot to retain the foot of the patient within a defined area. The more successful of the prior art machines secure the patient by providing padded ankle and instep cuffs for each foot, designed to fit, if desired, above the shoe worn by the patient in order to minimize and reduce trauma in the leg, ankle, instep and heel areas of the foot. One such version is shown in my pending U.S. patent application Ser. No. 251,484, filed Apr. 6, 1981, now U.S. Pat. No. 4,367,731.

SUMMARY OF THE INVENTION

The present invention departs from the principle of suspending the patient in an inclined or inverted position by the use of stocks, clamps, leg cuffs, ankle pads, instep pads, heel braces or pads over the top of the foot. Instead, the present invention employs a comfortably fitting, high-top shoe into which the foot, heel, ankle and instep area are inserted and secured. A structural re-enforcing member is designed as a part of the arch-heel area of the shoe from which a supporting attachment or linkage member is connected to carry the load or weight of the patient when the patient is inclined or inverted. The re-enforcing member of the shoe, with its attachment or linkage member, is designed for removable coupling to a rigid, supporting structure, such as a horizontal bar or tiltable bed. In the inverted position the patient is suspended from the shoe while the sole, arch and heel area of the shoe is physically retained in a secured position relative to the supporting structure or frame. The weight of the patient is distributed over the top area of the shoe and around the portion of the shoe that surrounds the instep, ankle, heel and lower leg portion.

The preferred embodiment employs a form-fitting, high-top shoe, similar in part to an ice skating or roller skating shoe. A strong re-enforcing plate is designed into or attached to the heel-arch area of the shoe for supporting a pivoted, inverted U-shaped member to which a hook member is securely attached. The hook member, positioned in front of and spaced apart from the ankle area of the foot, is retained in position by means of a strap or clamp attachable around the leg and above the ankle of the user. Both the U-shaped member and the hook member are spaced apart from the top portions of the shoe to prevent the forces acting upon the shoe, when the user is in an inverted position, from bearing upon the under side of the U-shaped and hook members. The hook member is removably attachable to a horizontal supporting bar. When the user is inverted, the forces acting upon the shoe are transmitted to the re-enforcing plate and on to the U-shaped member into the hook member. These forces are then carried by the hook member on to the horizontal supporting bar. The U-shaped member, along with the attached hook, is pivotally attached about a horizontal axis to the re-enforcing plate to enable both hook and U-shaped members to pivot forward of the foot to allow the foot to be easily inserted into the shoe.

Accordingly, a principal object of the invention is to provide a device for comfortably supporting the human body in an inverted position.

Another object is to provide a form-fitting shoe device for suspending the human body in an inverted position from the sole-heel area of the shoe.

Still another object of the invention is to provide a shoe device having a hook pivotally attached to the sole area of the shoe for holding the human body in an inverted position.

Yet another object is to provide an inversion shoe that is safer, easier to use and attractive in appearance.

DESCRIPTION OF THE INVENTION

Figure 1:
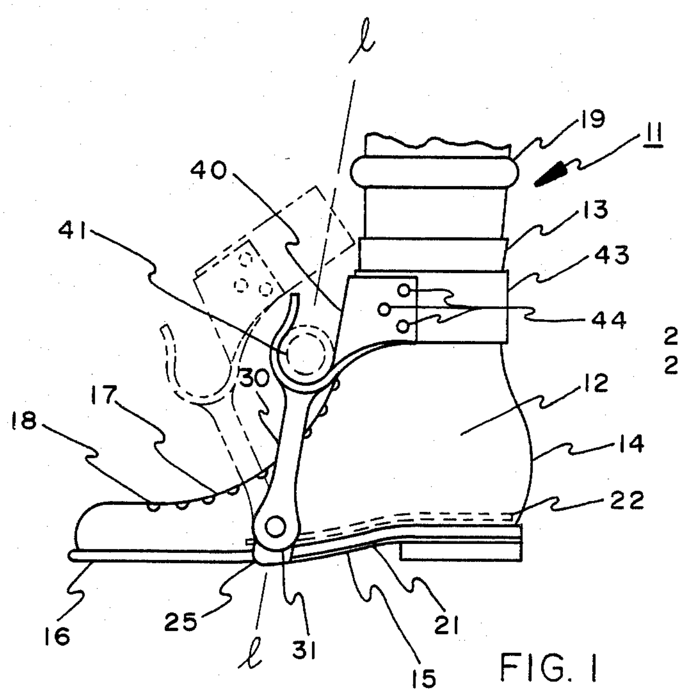
FIG. 1 illustrates the side view of the preferred embodiment of the inversion shoe of the invention.
Figure 2:
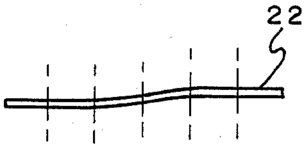
FIG. 2 shows the side view of the inner structural plate of the re-enforcing member of the inversion shoe.
Figure 4:
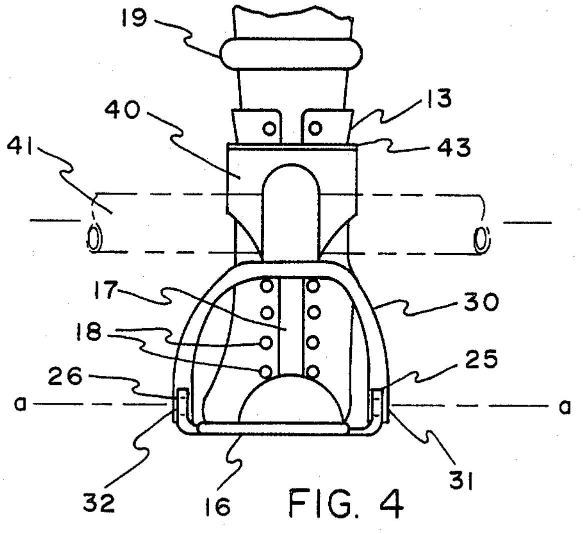
FIG. 4 is a front view of the preferred inversion shoe of FIG. 1.
Figure 7:
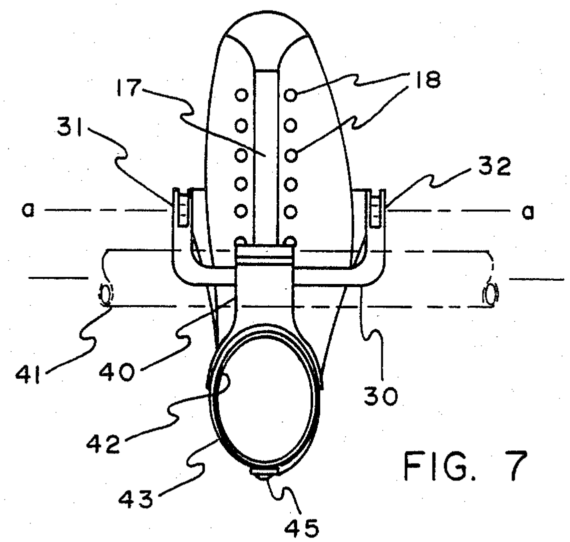
FIG. 7 is a top view of the inversion shoe of FIGS. 1 and 4.

Referring to the preferred embodiment of the invention 11 as illustrated in FIGS. 1, 4 and 7, there is shown a high-top, form-fitting shoe 12 constructed of leather, polymer or other suitable material for comfortably securing the instep, ankle, heel, leg and top portion of the foot of the user. As shown, the upper area 13 of shoe 12, along with the heel area 14, is shaped to conform to the leg and heel of the user. Similarly, the arch area 15 is likewise shaped to comfortably fit the arch of the foot. Shoe 12 includes a flexible sole 16, thereby enabling the user to walk in the shoe 12 in the normal fashion.

The top portion or area 17 of shoe 12 is designed to be securely attached over the top portion of the foot in the usual manner, as by lacing or other suitable means, and holes 18 are provided for shoe laces (not shown) for lacing the shoe.

The sole, arch and heel portions of the shoe are securely attached to the top or upper areas of the shoe, as by stitching, glueing or other suitable means. A preferred construction of shoe 12 is by molding whereby the entire shoe is composed of the same material. Shoes of this construction are well known, and one such form-fitting shoe is molded of resilient polymer material for use as a roller skating shoe. A sock 19 or other suitable liner may be worn by the user, if desired.

Figure 6:
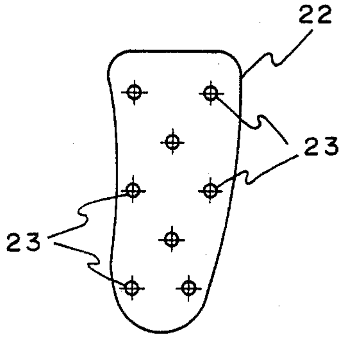
FIG. 6 is a top view of the inner structural plate of FIGS. 2 and 5.
Figure 8:
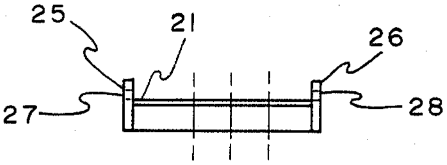
FIG. 8 is a front view of the external structural plate of FIG. 3.
Figure 9:
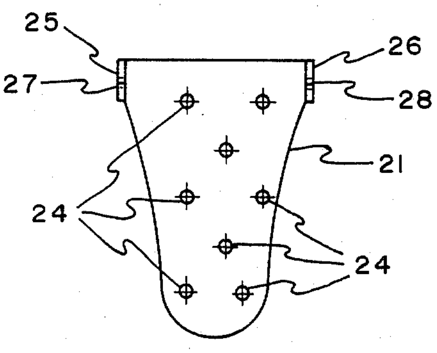
FIG. 9 is a top view of the external structural plate of FIGS. 3 and 8.

Shoe 12 is provided with re-enforcing member means consisting of an external or first shaped plate 21 and an inner or second shaped plate 22, as shown in FIGS. 2, 3, 5, 6, 8 and 9. Inner plate 22 is located within shoe 12 in the heel-arch area, as shown, and is provided with a group of eight holes 23, as seen in FIG. 6, for securing inner plate 22 to the shoe, as by glueing or by means of rivets. External plate 21 is attached below shoe 12 in the heel-arch area, as shown. Plate 21 is provided with a matching set of eight holes 24, as shown in FIG. 9, for securing plate 21 to shoe 12. Plate 21 is, preferably, secured to the heel-arch area by adhesive as well as by rivets coupled between plates 21 and 22 and passing through the matching holes 23 and 24 and the heel-arch area of shoe 12. Both re-enforcing plates 21 and 22 are shaped, as shown, and formed of steel or other material of suitable strength.

Figure 3:
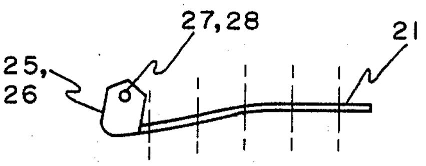
FIG. 3 illustrates the side view of the external sturctural plate of the re-enforcing member.
Figure 5:
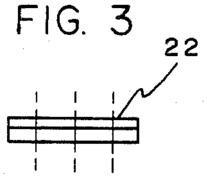
FIG. 5 is a front view of the inner structural plate of FIG. 2.

External re-enforcing plate 21 is provided with a pair of upwardly extending tabs 25 and 26 formed as by bending. Each tap 25 and 26 includes, respectively, holes 27 and 28, as seen in FIG. 3, for receiving a bushing or bolt. The upwardly extending tabs are located, respectively, on opposite sides of shoe 12 in the forward portion of the arch area of the shoe, as shown in FIG. 4.

An inverted U-shaped member 30, similar in part to a stirrup, is located in front of shoe 12. The lower ends 31 and 32 of U-shaped member 30 are pivotally attached to tabs 25 and 26 by means of bolts or screws passing through the holes 27 and 28, as shown in FIGS. 1, 4 and 7. If desired, the lower ends 31 and 32 may be forked, as shown, so as to straddle the tabs 25 and 26.

The manner by which the inverted U-shaped member 30 is pivotally attached to the external re-enforcing plate 21 may be similar to that used in conventional prosthetic devices to provide for a strong, pivotal support for U-shaped member 30 on re-enforcing plate 21. This form of attachment employs an internally threaded bushing extending through the lower end 31, 32 of U-shaped member 30 and through the holes 27 or 28 of tab 25 or 26. An oval-head type machine screw engages the internal threads of the bushing to securely retain inverted U-shaped member 30 pivotally attached to the tabs 25 and 26 of the external re-enforcing plate 21.

Securely attached to the top or apex of inverted U-shaped member 30 is a hook member 40 shaped, as shown, for detachable engagement to a horizontal, cylindrical support bar 41, shown by dotted lines in FIGS. 1, 4 and 7. The inner surface portion 42 of hook member 40 adjacent shoe 12 is further shaped to fit partially around the front area of shoe 12 and, accordingly, around the lower leg portion of the user, as shown in FIGS. 4 and 7. A leather strap 43 or other suitable means is attached to the inside surface portion 42 of hook member 40 to enable the user to secure hook member 40 to the leg of the user as by surrounding the upper portion of shoe 12. Leather strap 43 may be secured to the inner surface of portion 42 by adhesive or by rivets 44, as shown in FIG. 1. Strap 43 surrounds the upper portion of shoe 12 and, accordingly, the leg of the user above the ankle area and may be retained by means of a buckle (not shown) or other suitable means. in FIG. 7 the leather strap is secured behind shoe 12 and above the heel area 14 by a safety snap 45. Upon release of leather strap 43, hook member 40, along with inverted U-shaped member 30, may be pivoted forward of shoe 12 about the pivot axis a—a, as shown by the broken lines in FIGS. 4 and 7. This enables the user to easily insert the foot into shoe 12 and to lace shoe 12 to firmly grip and support the instep, ankle and heel areas of the foot.

The amount by which inverted U-shaped member 30 and hook member 40 may be pivoted forward of shoe 12 may be determined by the triangular shape of the upper tip 46 of taps 25 and 26 of external plate 21. This triangular-shaped tip 46 serves as a limit stop in cooperation with the inner surface of the lower forked ends 31, 32 of U-shaped member 30 to limit both the forward, as well as the rearward, pivoting of members 30 and 40.

While the inversion shoe 12 of FIGS. 1, 4 and 7 is shown in the upright position for ease of illustration, it will be appreciated that when the user is suspended in the inverted position he will be held in this position by the horizontal support bar 41. In this inverted position, shoe 12 will be inverted from the position shown in FIGS. 1 and 4.

The location of the pivot axis a—a in the forward area of the arch of shoe 12 causes the weight of the user, when inverted, to fall along an imaginary line 1—1 which passes through the center of hook member 40 and through the pivot axis a—a. The imaginary line 1—1 extends in the direction of and passes substantially through the center of gravity of the body of the user. This design feature substantially reduces the lateral forces acting upon hook member 40 in the direction of the leg of the user and minimizes the forces pressing against the upper portion 13 of shoe 12. Accordingly, the strength of leather strap 43 need not be great to safely secure hook member 40 to the upper area 13 of shoe 12 and to the leg of the user.

Figure 10:
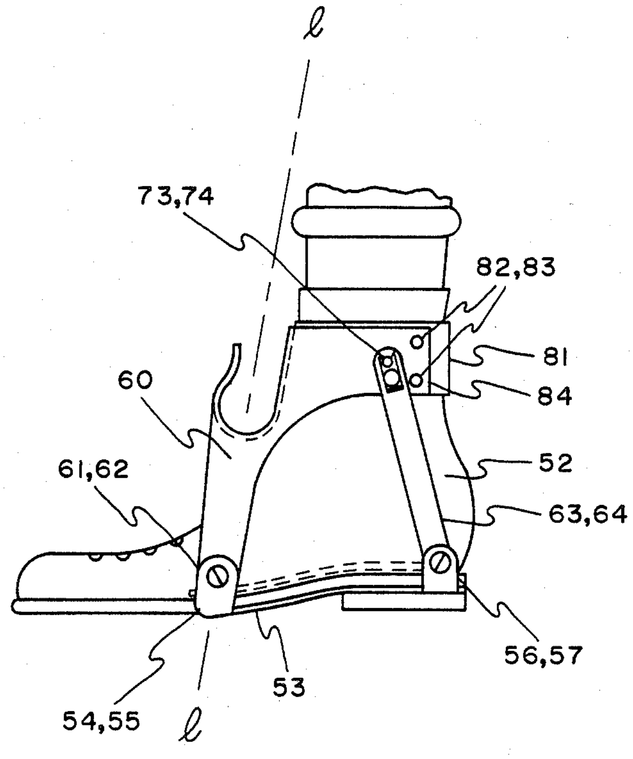
FIG. 10 is a side view of an alternative embodiment of the inversion shoe of the invention.
Figure 11:
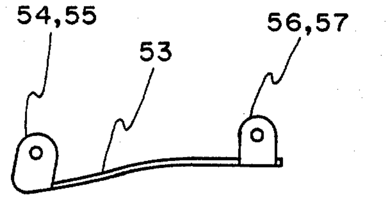
FIG. 11 is a side view of the external plate of the re-enforcing member for the inversion shoe of FIG. 10.

The embodiment of the invention illustrated in FIG. 10 employs a shoe 52, similar in most respects to shoe 12 of the preferred embodiment. The re-enforcing means, however, includes an external shaped plate 53 provided with two sets of upwardly extending tabs 54,55 and 56,57, as shown in FIG. 11. The first set of tabs 54,55 is located in the front or forward area of the arch, one being positioned on each side of shoe 52, while the second set 56,57 is positioned near the rear and on each side of the heel. The inner shaped plate located within shoe 52 may be the same as employed in the preferred embodiment. The inner shaped plate and the external shaped plate 53 are firmly secured to shoe 52 by adhesive and by rivets (not shown).

An inverted U-shaped member and hook member 60 integrally formed of the same material, as by stamping or shaping, is pivotally attached, at its lower ends 61,62, to the forward, upwardly extending tabs 54,55 in any suitable manner. The integrally formed U-shaped member and hook member 60 provides the same function as hook member 40 of the preferred embodiment, and is adapted for removable attachment to a cylindrical, horizontal support bar.

Figure 12:
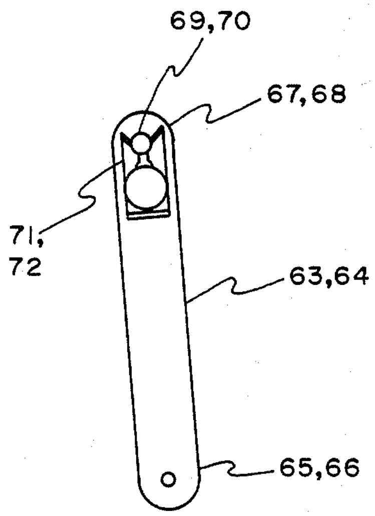
FIG. 12 is a view of the linkage member used with the inversion shoe of FIG. 10 showing the snap sliding latch.

The integral U-shaped member and hook member 60 may be secured and locked in the position shown in FIG. 10 by a pair of linkage members 63, 64 located, respectively, on each side of shoe 52. The lower ends 65, 66 of each linkage member are pivotally attached, respectively, to the second set of upwardly extending tabs 56, 57. The upper ends 67, 68 of each linkage member are provided, respectively, with holes 69, 70 cooperating with a conventional sliding latch means 71, 72, as seen in FIG. 12.

A pair of detented studs 73, 74 extend, respectively, from each side of member 60 at a position above the ankle area. Studs 73, 74 are rigidly attached to member 60 and are adapted for receiving the upper ends 67, 68, respectively, by passing through the holes 69, 70 when the sliding latch is in its down or unlocked position. When linkage members 63, 64 are in the engaged position, the jaws of the sliding latch means 71, 72 engage and snap around the detented studs 73, 74, respectively, to secure the U-shaped and hook member 60 in a rigid and locked position.

A strip of leather or other suitable material 81 is placed on the inside of the upper portion of member 60 that partially surrounds the upper portion of shoe 52 to prevent or reduce wear upon this region of shoe 52. A pair of holes 82, 83 extending through member 60 are located at the upper rear end 84 of member 60 near the detented studs 73, 74. A similar pair of holes are located on the opposite side of member 60. These holes are adapted for receiving lacing cords (not shown) drawn around the rear of shoe 52 and above the heel to retain shoe 52, and, accordingly, the leg of the user into the position as shown.

Disengagement or release of the sliding latch means 71, 72 and removal of the upper ends 67 and 68 of the linkage member 63, 64 from the detented studs 73, 74 allows the U-shaped and hook member 60 to be pivoted forward of shoe 52 so that the foot of the user may be easily inserted into shoe 52.

The integral U-shaped and hook member 60 should be formed of strong material and may be cut, stamped and formed of steel, if desired. The re-enforcing means, including the inner plate and the external plate 53, may be similarly formed. Alternatively, U-shaped and hook member 60 may be molded of a strong and rigid plastic or polymer material, if desired.

When the user is inverted, the weight acting upon the U-shaped and hook member 60 falls along an imaginary line 1—1 passing through the center of hook member 60 and the pivot axis of the tabs 54, 55 in the same general manner as described in connection with the preferred embodiment of FIGS. 1, 4 and 7.

Figure 13:
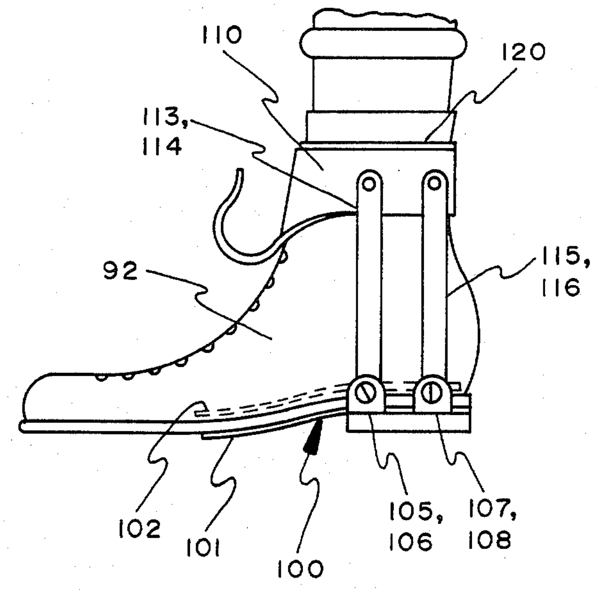
FIGS. 13 and 14 are side views of a further embodiment of the inversion shoe of the invention.
Figure 14:
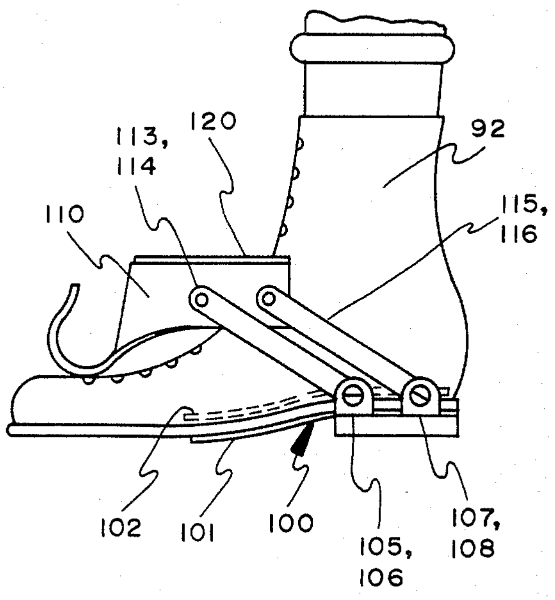

The embodiment of the invention illustrated in FIGS. 13 and 14 employs a high-top, form-fitting shoe 92 substantially identical to the shoe employed in the above-described embodiments. The re-enforcing means 100 includes an external shaped plate 101 and an internal plate 102 secured to each other through the heel-arch area of the shoe by any suitable means, such as rivets. External plate 101 includes two pairs of upwardly extending tabs 105, 106 and 107, 108, located, respectively, on opposite sides of shoe 92 below the heel area.

A hook member 110 is pivotally supported in the positions shown in FIGS. 13 and 14 by two pairs of linkage members 113, 114 and 115, 116, located, respectively, on opposite sides of shoe 92 in the heel-ankle area. The lower ends of each pair of linkage members are pivotally attached, respectively, to taps 105, 106 and 107, 108, as shown. The upper ends of each pair of linkage members are pivotally attached, respectively, to each side of hook member 110. A pad of suitable material 120 is attached to the inside surface of the portion of hook member 110 that partially surrounds the upper portion of shoe 92 and the leg of the user. Hook 110 is secured to the leg of the user by any suitable safety latch, buckle or other means attached to the rear portion of hook 110 for surrounding the rear portion of the leg of the user.

Hook member 110 may be moved forward and downward, when not secured, to the position shown in FIG. 14 to enable the user to readily insert the foot into shoe 92.

When the user is inverted, the weight is transmitted from shoe 92 into the re-enforcing means 100 and through the two pairs of linkage members 113, 114 and 115, 116 on to hook member 110. The forces on hook member 110 are carried by a horizontal support bar or other suitable supporting structure, in the same manner as described above.

Each of the embodiments of the inversion shoe of the invention includes a comfortable, form-fitting shoe for securing the foot, heel, ankle, instep and lower leg portions of the user. The re-enforcing means in the sole-heel area of the shoe transfers the load carried by the shoe through a pivotal linkage structure on to a hook member located in front of the shoe and above the ankle area. The hook member is supported so as not to bear down upon the top or instep area of the shoe and, accordingly, the top portion of the foot of the user. When matching pairs of inversion shoes are worn by the user, he may be comfortably and safely secured in an inclined or inverted position without the trauma experiemced with the prior art devices.

Since many changes may be made in the above-described apparatus and many different embodiments of this invention could be made without departing from the scope thereof, it is intended that all matter contained in the above description or shown in the accompanying drawings shall be interpreted as illustrative and not in a limiting sense.

What is claimed is:

1. A device for suspending a human body in an inverted position with respect to a horizontally extending supporting structure, comprising in combination:

(a) shoe means adapted for receiving and securing the foot of the human body, said shoe means including re-enforcing means in the heel-arch area of said shoe means, said shoe means with re-enforcing means being of sufficient strength for holding the human body in an inverted position;

(b) a rigid, inverted U-shaped member positioned above the top of said shoe means, said inverted U-shaped member spanning the width of said shoe means from the left to the right side, said inverted U-shaped member having left and right lower ends pivotally attached to said re-enforcing means for movement about a pivot axis extending from the left to the right sides of said shoe means; and (c) a rigid, U-shaped hook means attached to the apex of and forming a part of said rigid, inverted U-shaped member, said U-shaped hook means and said inverted U-shaped member being pivotally movable over the top portion of said shoe means about said pivot axis, said U-shaped hook means being adapted for removable attachment to a horizontally extending supporting structure for suspending said shoe means and the human body in an inverted position.

2. The device as defined by claim 1 further including means attached to said hook means for surrounding the leg of the human body for securing said hook means and said inverted U-shaped member in a fixed position with respect to the leg.

3. The device as defined by claim 1 wherein said re-enforcing means includes a first plate member attached to the sole of said shoe means in the heel-arch area externally of said shoe means and a second plate member situated within said shoe means in the heel-arch area, said first and second plate members being secured to each other through the heel-arch area of said shoe means.

4. The device as defined by claim 1 wherein said shoe means is composed of resilient polymer material and wherein the sole and top portions of said shoe means are integrally formed to provide a strong, comfortable fit to the foot of the human body.

5. The device as defined by claim 4 wherein said re-enforcing means is formed integrally with said shoe means.

6. The device as defined by claim 1 wherein said inverted U-shaped member and said hook means are integrally formed of the same material.

7. The device as defined by claim 1 further comprising a first linkage member having upper and lower ends and a second linkage member having upper and lower ends, said first and second linkage members being located on opposite sides of said shoe means, the lower end of said first linkage member being pivotally attached to said re-enforcing means in the heel area on one side of said shoe means, the lower end of said second linkage member being pivotally attached to said re-enforcing means in the heel area on the opposite side of said shoe means, the upper ends of said first and second linkage members being adapted for removable attachment to said hook means.

8. A device for suspending a human body in an inverted position with respect to a horizontally extending supporting structure, comprising in combination:

(a) shoe means adapted for receiving and securing the foot of the human body, said shoe means including re-enforcing plate means in the heel-arch area of said shoe means of sufficient strength for holding said shoe means and the human body in an inverted position;

(b) a rigid U-shaped hook member located above the top surface of said shoe means, said rigid U-shaped hook member having front and rear upwardly extending portions and a rounded bottom portion;

(c) left and right rigid support members located, respectively, on the left and right sides of said shoe means, said left and right rigid support members having left and right lower end portions pivotally attached to said re-enforcing plate means for movement about a pivot axis extending from the left to the right sides of said shoe means, said left and right rigid support members having left and right upper end portions attached to said rigid U-shaped hook members, said rigid U-shaped hook member being pivotally movable over the top portion of said shoe means about said pivot axis, the pivotal movement of said rigid U-shaped hook member moving the rear upwardly extending portion of said rigid U-shaped member from a first position adjacent the front leg portion of said shoe means to a second position above the top of the foot of said shoe means to enable the foot of the user to be inserted within the shoe; and (d) means attached to said rigid U-shaped hook member for holding the rear upwardly extending portion of said rigid U-shaped hook member in a position adjacent the leg portion of said shoe means when said shoe means is to be inverted, said rigid U-shaped hook member being adapted for removable attachment to a horizontally extending support structure for suspending said shoe means and the human body in an inverted position.

9. The device as defined by claim 8 further comprising additional left and right rigid support members located, respectively, on the left and right sides of said shoe means, said additional left and right rigid support members having left and right lower end portions pivotally attached to said re-enforcing plate means in the heel area of said shoe means for movement about a second pivot axis extending from the left to the right sides of said shoe means, said additional left and right rigid support members having left and right upper end portions adapted for attachment to said rigid U-shaped hook member.

10. The device as defined by claim 9 wherein the left and right upper end portions of said additional left and right rigid support members are pivotally attached to said rigid U-shaped hook member.

* * * * *